United States Patent [19]

Weilbacher et al.

[11] Patent Number: 4,994,050
[45] Date of Patent: Feb. 19, 1991

[54] FLOAT CHAMBER AND SLEEVE FOR USE IN A CHEST DRAINAGE DEVICE

[75] Inventors: Eugene E. Weilbacher, Ellisville; F. Thane DeWeese, Ladue, both of Mo.

[73] Assignee: Sherwood Medical Company, St. Louis, Mo.

[21] Appl. No.: 429,892

[22] Filed: Oct. 31, 1989

[51] Int. Cl.$^5$ .............................................. A61M 1/00
[52] U.S. Cl. .................... 604/320; 604/319; 604/321; 604/119; 137/205
[58] Field of Search ............. 604/319, 320, 321, 318, 604/317; 137/205; 116/228

[56] References Cited

U.S. PATENT DOCUMENTS

| | | |
|---|---|---|
| 3,683,913 | 8/1972 | Kurtz et al. . |
| 3,809,085 | 5/1974 | Bidwell et al. . |
| 3,960,165 | 6/1976 | Holbrook et al. . |
| 4,195,633 | 4/1980 | Nehring et al. . |
| 4,289,158 | 9/1981 | Nehring . |
| 4,402,687 | 9/1983 | Denty et al. ................... 604/319 |
| 4,439,189 | 5/1984 | Sargeant et al. . |
| 4,439,190 | 3/1984 | Protzmann et al. . |
| 4,455,141 | 6/1984 | Todd . |
| 4,519,796 | 5/1985 | Russo . |
| 4,540,413 | 9/1985 | Russo ........................... 604/320 |
| 4,601,715 | 7/1986 | Olson . |
| 4,650,476 | 3/1987 | Telang ........................... 604/319 |
| 4,650,477 | 3/1987 | Johnson . |
| 4,767,417 | 8/1988 | Boehringer et al. . |
| 4,781,707 | 11/1988 | Boehringer et al. . |
| 4,784,642 | 11/1988 | Everett, Jr. et al. . |
| 4,911,697 | 3/1990 | Kerwin .......................... 604/319 |
| 4,955,874 | 9/1990 | Farrar et al. ................... 604/319 |

*Primary Examiner*—Richard J. Apley
*Assistant Examiner*—Lynne A. Reichard
*Attorney, Agent, or Firm*—Andrew J. Beck; Montgomery W. Smith; Richard D. Allison

[57] ABSTRACT

A chest drainage device having a collection chamber, a water seal chamber and a suction control chamber wherein the suction control chamber includes first and second columns wherein the top end of the first column is open to the atmosphere and the top end of the second column is in flow communication with a vacuum source and water seal chamber and wherein the bottom end of the first and second columns are in flow communication with a float chamber and ballast sleeve to increase the effective dynamic water height of liquid in the suction control chamber and to decrease the overall height of the suction control chamber of the chest drainage device while maintaining the same operational vacuum pressure range as previous chest drainage devices.

27 Claims, 2 Drawing Sheets

FLOAT CHAMBER AND SLEEVE FOR USE IN A CHEST DRAINAGE DEVICE

FIELD OF THE INVENTION

This invention relates to chest drainage devices and more particularly to an improved suction control chamber design wherein the overall height of the chest drainage unit may be reduced while allowing the suction control chamber to produce the desired negative pressure in the patient's pleural cavity.

BACKGROUND

The present invention is related to U.S. Pat. application Ser. No. 07/363,749 filed on June 9, 1989 entitled "Floatation Chamber For Use In A Chest Drainage Device" assigned to a common assignee Sherwood Medical Company and incorporated herein by reference. The present invention relates to an improvement over the prior application wherein the operational range of a chest drainage device constructed according to the present invention may be increased.

Chest drainage devices for removing fluids from the pleural cavity of a patient generally include a collection chamber, a water seal chamber and a suction control chamber. The suction control chamber operates to limit the negative pressure applied to the collection chamber and the pleural cavity of the patient. During the operation of a chest drainage device, liquid from the patient's pleural cavity is drawn into and accumulated in the collection chamber. Gases are drawn from the pleural cavity of the patient and pass through a water seal in the water seal chamber to the source of suction. The water seal operates as a barrier to prevent the patient's pleural cavity from being exposed to the atmosphere and also prevents the patient's pleural cavity from being in direct flow of communication with the vacuum source.

U.S. Pat. No. 3,783,870, issued to Schachet on Jan. 8, 1974, and U.S. Pat. No. 4,439,190, issued to Protzmann et al on Mar. 27, 1984 describe the operation of a typical chest drainage device, both of which are incorporated herein by reference. The present invention is readily adaptable for use in an integral one-piece chest drainage device or a multi-bottle chest drainage device similar to the chest drainage devices referenced above. Generally, the suction control chamber allows the user to apply a prescribed vacuum pressure to the pleural cavity of a patient by adding a predetermined amount of liquid to the suction control chamber. The commonly used chest drainage device utilizes a suction control chamber which is basically an unequal-legged water manometer to regulate the suction pressure being applied to the pleural cavity of a patient. This type of suction control chamber generally consists of a pair of legs or columns interconnected at their bottom ends. The top of the generally smaller, first column, is open to the atmosphere. The second column is generally larger than the first column and includes a top end in flow communication with the vacuum source and the pleural cavity of the patient.

The overall height of the suction control chamber typically dictates the minimum height of the chest drainage device. Commonly available chest drainage devices have an overall height of approximately 40 cm. In the typical suction control chamber, approximately 25 cm. is attributable to the operational range of the chest drainage device. The remaining height of the chest drainage device is attributable to the air/water separation space located above the water fill level and the height of the base or stand of the chest drainage device.

The effectiveness of the air/water separation space at any given air flow rate is determined by the over all suction control chamber geometry and the height of the suction control chamber above the liquid level. If the air flow rate through the suction control chamber is too high, liquid is entrained in the air and will be carried out of the suction control chamber. If this occurs, the vacuum pressure being applied to pleural cavity of the patient will gradually decrease as the liquid level in the suction control chamber is depleted. Additionally, the liquid from the suction control chamber may contaminate the vacuum source and/or be deposited within other chambers of the chest drainage device. Certain chest drainage devices have incorporated baffles in the top of the suction control chamber in an effort to decrease the required height of the air/water separation space and to prevent the loss of water in the suction control chamber.

In a chest drainage device, the pressure applied to the pleural cavity of the patient is dependent on the dynamic water height of the liquid in the suction control chamber. For example, if the desired patient pressure is 20 cm. $H_2O$ of vacuum pressure, a dynamic water height of at least 20 cm. is required in the suction control chamber. In chest drainage devices which utilize a water seal chamber, the water seal chamber will typically add approximately 2 cm. $H_2O$ of resistance so that if the desired patient pressure is 20 cm. $H_2O$, the suction control chamber must provide 22 cm. $H_2O$ of vacuum pressure to overcome the resistance of the water seal chamber. The standard operating ranges for most chest drainage devices is between 5 and 25 cm. $H_2O$ vacuum pressure. Therefore, in order to have the capability of supplying 25 cm. $H_2O$ of vacuum pressure to the pleural cavity of the patient, this portion of the suction control chamber must be at least 25 cm. high. The baffle systems used in certain chest drainage devices are designed to prevent liquid from being entrained in the air and may be used to reduce the height of the air/water separation space and do not materially effect the dynamic water height of the suction control chamber. Therefore, unless valves or other flow restricting devices are used, the height of a chest drainage device must be at least 25 cm. plus the height of the air/water space or baffle chamber and the base of the chest drainage device.

SUMMARY OF THE INVENTION

An object of the present invention is to provide an improved suction control chamber wherein the overall height of the chest drainage device may be reduced.

A further object of the present invention is to provide a chest drainage device wherein the actual vacuum pressures being applied to the patient are readily ascertainable.

Still another object of the present invention is to provide an improved suction control chamber which is readily adaptable for use in nearly any chest drainage device.

Still another object of the present invention is to provide a compact chest drainage device having an expanded and linear operational range.

In accordance with one form of the present invention, the improved chest drainage device is a type of chest drainage device typically known as a three-bottle chest drainage device. Thus, the improved chest drainage device of the present invention preferably includes a collection chamber adapted to be in fluid communication with the patient's pleural cavity; a water seal chamber in flow communication with the collection chamber; and an improved suction control chamber. Additionally, the illustrated form of the present invention includes a manifold which maintains flow communication among the various chambers of the chest drainage device.

The suction control chamber of the present invention is comprised of a pair of generally elongate columns in fluid communication at their bottom ends. The smaller, first column extends downwardly into the larger, second column. The top end of the first column is open to the atmosphere while the bottom end of the first column includes a moveable float chamber generally oriented in flow communication with the bottom opening of the first column. Additionally, an elongated sleeve is attached to the top of the float chamber to movably surround the first column.

In the preferred embodiment, the second column is larger than the first column and substantially encloses the first column. The top end of the second column is in flow communication with the vacuum source and the pleural cavity of the patient. The height of the second column is generally divisible into two sections, the first section is the air/water separation space and is located near the top end of the second column. The second section is the suction control section which extends from the bottom end of the suction control chamber upwardly to the air/water separation space. The suction control section is the portion of the suction control chamber which is typically pre-filled with liquid to create the dynamic water height which controls the amount of vacuum pressure actually being applied to the pleural cavity of the patient.

An advantage of the present invention is that the improved suction control chamber allows for the construction of a versatile chest drainage device which has either a smaller overall height than the presently available chest drainage devices or has a greater operational range than presently available chest drainage devices without increasing the height of the chest drainage device.

Another advantage of the present invention is that the operational range of the chest drainage device is linearly adjustable by adding or removing incremental amount of liquid from the suction control chamber.

Further advantage of the improved suction control chamber is that it is readily adaptable for use on nearly any chest drainage device.

These, as well as other features and advantages of the present invention will become apparent from the following detailed description and accompanying drawings.

DETAILED DESCRIPTION OF THE PREFERRED EMBODIMENT

Figure 1:
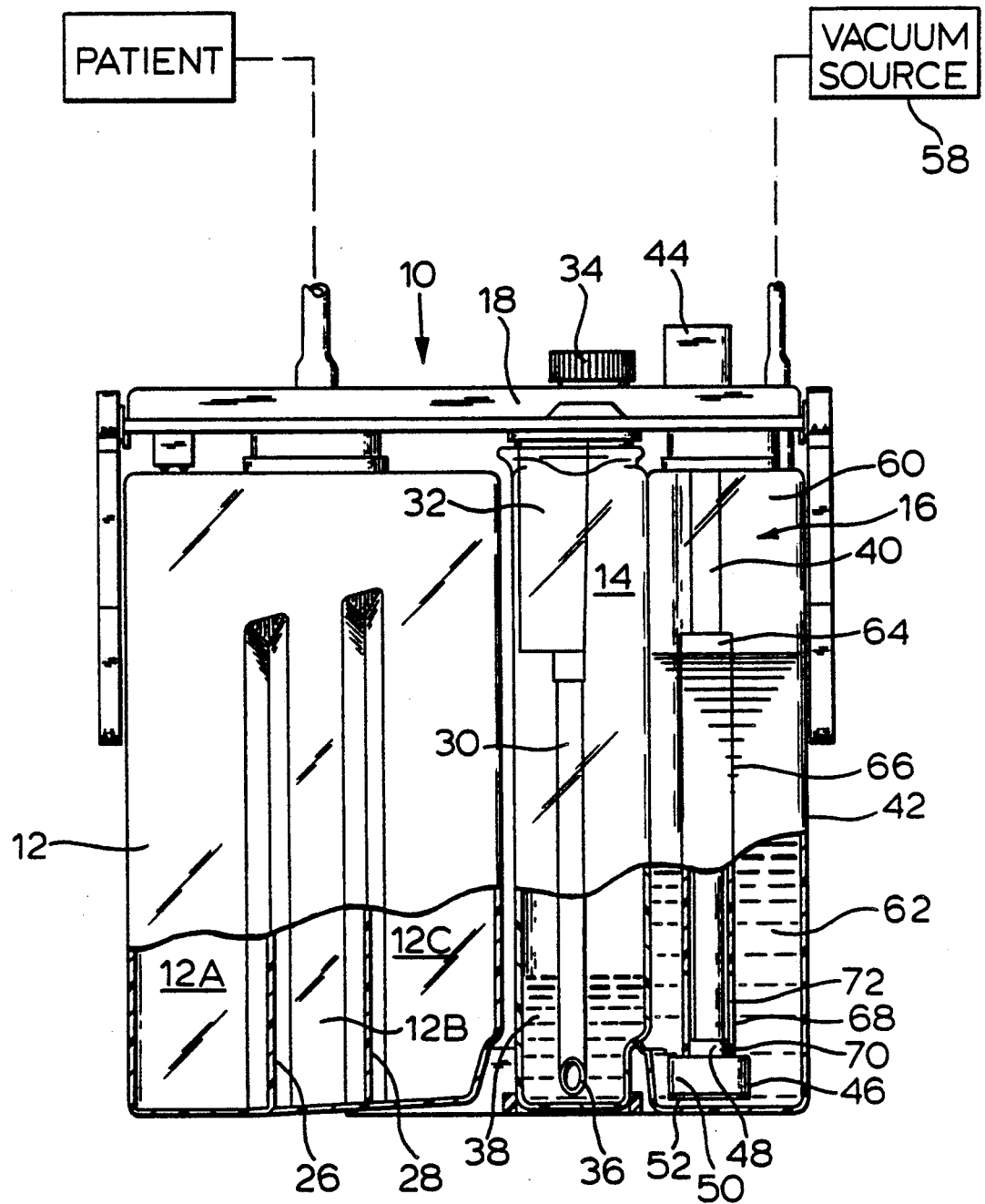
FIG. 1 is a cross-sectional side view of the preferred embodiment of the present invention.

A preferred design of the present invention is illustrated in the attached drawings and is designated herein, generally, as a chest drainage device 10. The chest drainage device 10 of the present invention consists generally of a collection chamber 12, a water seal chamber 14, a suction control chamber 16 and a manifold 18. In the preferred embodiment, the manifold 18 is attached to the top of the collection chamber 12 and the suction control chamber 16 is attached to the manifold 18 adjacent to the water seal chamber 14. The manifold 18 provides the desired flow communication between the collection chamber 12, the water seal chamber 14 and the suction control chamber 16, thus, eliminating the need for hoses, conduits and the like frequently used in a variety of other chest drainage devices.

In order to provide for the accurate measurement of the fluid collected from the pleural cavity of the patient, the collection chamber 12 is provided with inner walls 26 and 28, which, in combination with the outer walls 20, divide the collection chamber 12 into three compartments 12A, 12B and 12C. The height of wall 26 is less than the height of wall 28 so that once compartment 12A is filled, fluid will flow into compartment 12B. After compartment 12B is filled, fluid will spill over into compartment 12C. Each compartment has graduations thereon so that the attending physician or nurse can readily determine the amount of drainage collected from the pleural cavity of the patient.

The water seal chamber 14 includes a water seal column 30 and a baffle chamber 32. Liquid is poured into the water seal chamber 14 through the fill cap 34 until it reaches the fill line indicated on the side of the water seal chamber 14. The volume of liquid placed in the water seal chamber 14 should be sufficient to continuously cover the bottom opening 36 of the water seal column 30 during the typical operation of the chest drainage device 10. This volume of liquid is commonly known as the water seal and is referred to herein as the water seal 38.

The suction control chamber 16 includes a generally elongate cylindrical first column 40 which is surrounded and substantially enclosed by a larger second column 42. The top end of the first column 40 includes a fill opening 44 which is open to the atmosphere and allows liquid to be readily added to the suction control chamber 16. The first column 40 extends downwardly into the suction control chamber 16 from the fill opening 44 to a float chamber 46 which movably contacts the open bottom end of the first column 40. A ballast sleeve 64 is attached to the top of the float chamber 46 and extends upwardly along the first column 40.

The float chamber 46 consists of a retaining ridge 48 on the top surface thereof; a body section 50 and a lower base section 52. The body section 50 includes a centrally positioned recess 56 which slidably receives the bottom end of the first column 40. The inner diameter of the recess 56 is slightly larger than the outer diameter of the first column 40 to allow air to pass therebetween. The retaining ridge 48 extends upwardly from the body section 50 to further retain the first column 40 therein and to maintain the float chamber 46 in a slidable, generally contacting relation with the bottom end of the first column 40. The body section 50 and the base section 52 cooperate to create a float chamber 46 having a precisely defined buoyancy by retaining a specific amount of air therein.

The second column 42 includes a top end in flow communication with the vacuum source 58 and the pleural cavity of the patient through a variety of passageways in the manifold 18. The bottom end of the second column 42 is in flow communication with the bottom end of the first column 40 and the float chamber 46. The second column 42 is generally divisible into two sections; the top section is the air/water separation space 60 and the lower, second section, is the suction control section 62. The air/water separation space 60 operates to prevent liquid from being drawn into the vacuum source 58 or into the collection chamber 12 of the chest drainage device 10. The height of the air/water space 60 in the preferred embodiment, is typically 10 to 17 centimeters high and may be reduced through the use of a variety of baffles (not shown) or by modifying the overall geometry of the suction control chamber 16.

The lower section of the second column 42 is the suction control section 62. This section of the second column 42 creates the dynamic water height of the liquid in the suction control chamber 16 and determines the amount of vacuum pressure actually applied to the pleural cavity of the patient. The typical chest drainage device applies between 5 and 25 cm. to the pleural cavity of the patient and therefore the minimum height of the suction control section 62 is typically 25 cm. In the present invention, when liquid is added to the suction control chamber 16, the volume and buoyancy of the float chamber 46 decreases the amount of liquid necessary to create the desired dynamic water height and therefore reduces the overall height of the suction control section 62. The addition of the ballast sleeve 64 to the float chamber 46 allows the patient suction pressure to be adjusted linearly so that the patient vacuum pressure may be increased or decreased by adding or removing an incremental amount of liquid to the suction control chamber 16.

For example, in the typical suction control chamber 16, liquid is added to the bottom of the suction control chamber 16 to a desired level corresponding to the amount of vacuum pressure to be applied to the pleural cavity of the patient. This is commonly known as the dynamic water height of the suction control chamber. Liquid from the second column 42 of the suction control chamber 16 flows into the first column 40 until the magnitude of the difference in fluid levels between the second column 42 and the first column 40 equals the magnitude of the pressure difference between the pressure in the suction control chamber 16 and atmospheric pressure, which pushes on the fluid in the first column 40. During the operation of a chest drainage device 10, the vacuum source 58 applies a vacuum pressure to the top of the second column 42 and causes the liquid to be drawn from the first column 40 into the bottom of the second column 42. As this occurs, air is pushed by atmospheric pressure into the suction control chamber 16 through the first column 40 and into the second column 42 to offset the pressure difference between the dynamic water height of the column and the vacuum pressure being applied by the vacuum source 58.

The float chamber 46 of the present invention normally operates to apply a buoyancy pressure to the bottom opening of the first column 40. This buoyancy pressure is directed against the bottom of the first column 40 and provides an added pressure in addition to the dynamic water height of the suction control chamber 16 that must be over come before air is pushed into the suction control chamber 16. When the vacuum source 58 applies a vacuum pressure in excess of the dynamic water height of the suction control chamber 16 and the buoyancy pressure created by the float chamber 46, air is pushed into the suction control chamber 16 through the first column 40 to offset the difference. Therefore, if the liquid in the suction control chamber 16 provides a dynamic water height of approximately 15 cm. and the float chamber 46 applies a buoyancy pressure equivalent to 5 cm. $H_2O$, a vacuum pressure in excess of 20 cm. $H_2O$ will be required before air is pushed into the suction control chamber 16 through the first column 40 by the atmospheric pressure. Therefore, by decreasing the required dynamic water height of the suction control chamber 16 by 5 cm. the overall height of the suction control chamber 16 and chest drainage device 10 may also be reduced by approximately 5 centimeters.

This capability is also useful where it is desirable to increase the operational range of the suction control chamber 16 without increasing the overall height of the suction control chamber 16. In the past, it was necessary to add a separate vacuum regulator to the chest drainage device and bypass the suction control chamber 16 to obtain higher vacuum pressures. With the present invention, it is possible to design a suction control chamber 16 capable of applying higher vacuum pressures to the pleural cavity of the patient without significantly increasing the overall height of the suction control chamber 16 by using a float chamber 46 and ballast sleeve 64 of the type described herein.

Figure 2:
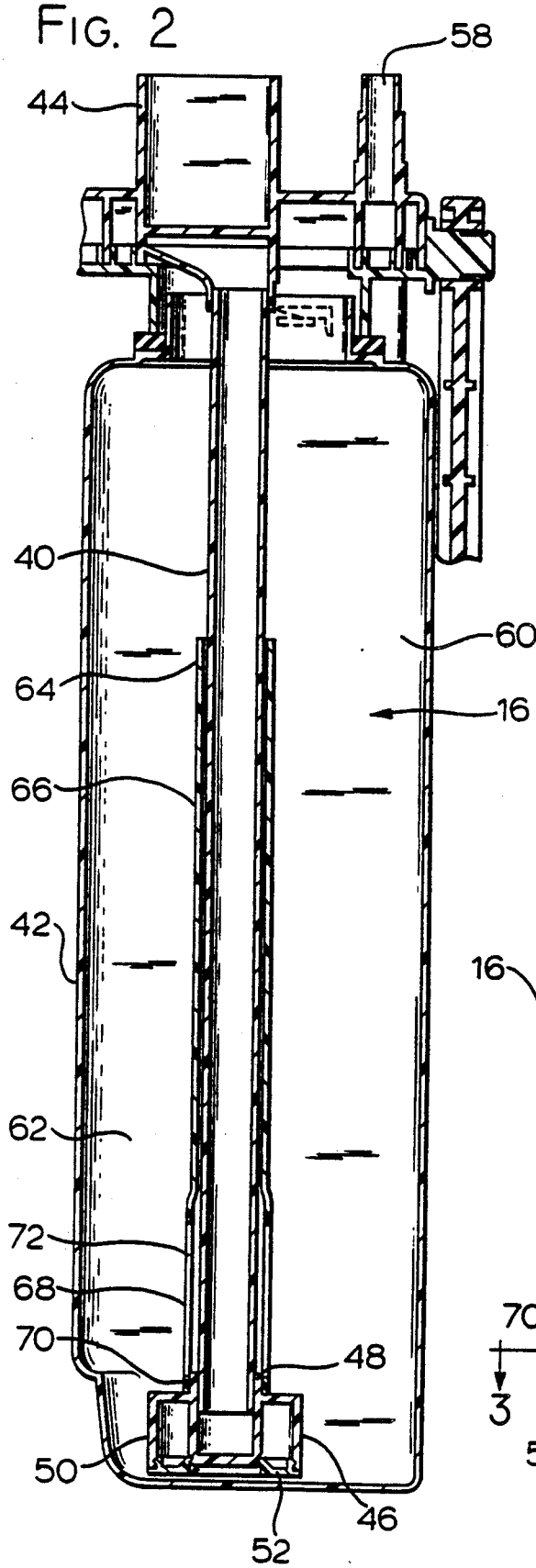
FIG. 2 is an enlarged cross-sectional view of the suction control chamber of the present invention.
Figure 3:
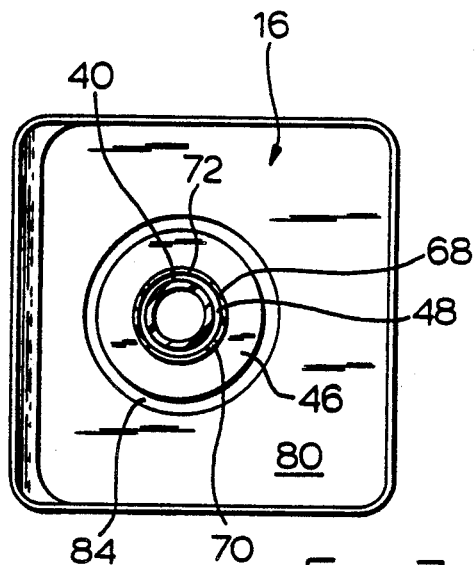
FIG. 3 is a cross-sectional view of an alternate embodiment of the present invention taken along lines 3—3 of FIG. 4.
Figure 4:
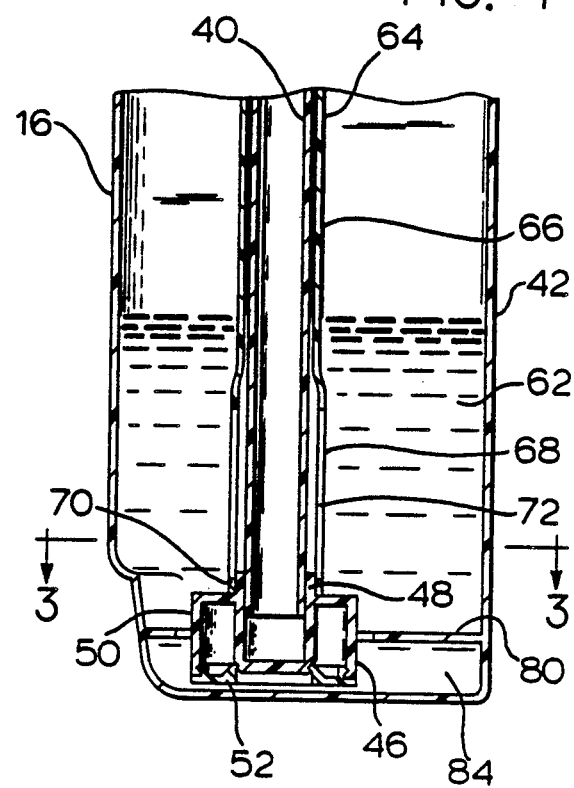
FIG. 4 is an enlarged cross-sectional view of the suction control chamber of the alternate embodiment of the present invention illustrated in FIG. 3.

As best illustrated in FIGS. 2 and 4, a ballast sleeve 64 is added to the float chamber 46 so that the pressure applied to the pleural cavity of the patient varies linearly during the operational range of the chest drainage device 10. The ballast sleeve 64 consists generally of a top, first second 66 and a lower, second second 68. The top section 66 is generally cylindrical and is designed to slidably surround nearly the entire length of the first column 40 without causing excess frictional resistance therebetween. The lower section 68 extends downwardly from the top section 66 and tapers outwardly to a ballast collar 70 which engages the retaining ridge 48 on the float chamber 46. The lower section 68 includes a pair of tapered openings 72 which are surrounded by a pair of extensions 74 that allow atmospheric air to pass from the bottom of the first column 40 and into the second column 42 through the tapered openings 72. The addition of the ballast sleeve 64 to the float chamber 46 allows the buoyancy pressure created by the relationship between the float chamber 46 and the ballast sleeve 64 to increase linearly with increases in the fluid level in the suction control chamber 16 and also allows the chest drainage device to operate at a lower initial vacuum pressure than is possible with the float chamber 46 alone.

FIG. 4 also illustrates the use of a damper 80 to create a substantially closed damper chamber 84 adjacent to the body section 50 of the float chamber 46. The use of the damper 80 will decrease pressure fluctuations caused by erratic movement between the float chamber 46 and the bottom of the first column 40. When the float chamber 46 moves downwardly from the bottom of the first column 40 to allow air to flow through the first column 40, liquid in the damper chamber 84 must be displaced to allow for the downward movement of the float chamber 46. In order for this to occur, liquid in the damper chamber 84 must flow around the sides of the float chamber 46 and past the damper 80. Likewise, when the float chamber 46 moves upwardly to prevent air from flowing through the first column 40, liquid must flow downwardly and into the area of the damper chamber 84 vacated by the float chamber 46.

As an example of the operation of the present invention, a dynamic water height of 7 cm. will produce a suction control chamber pressure of approximately 7 cm. $H_2O$ to create a patient vacuum pressure of approximately 5 cm. $H_2O$ when a water seal chamber 14 is used. At a dynamic water height of approximately 17 cm., a suction control chamber pressure of approximately 27 cm. $H_2O$ will be created to apply a vacuum pressure of approximately 25 cm. $H_2O$ to the pleural cavity of the patient when a water seal chamber 14 is used.

An important factor in the operation of the present invention is the portion of the ballast sleeve 64 which is present above the liquid level at any given time. The density of the ballast sleeve 64 is preferably at or near the density of water so that the submerged portion of the ballast sleeve 64 will not materially affect the buoyancy pressure created by the float chamber 46. The portion of the ballast sleeve 64 above the liquid level in the suction control chamber 16 will exert a downward pressure on the float chamber 46 to oppose the buoyancy pressure created by the submerged float chamber 46. Therefore, when the dynamic water height in the suction control chamber 16 is relatively small, the portion of the ballast sleeve 64 above the liquid level will exert a greater downward pressure to oppose the buoyancy pressure created by the float chamber 46. As the dynamic water height is increased, less of the ballast sleeve 64 will be above the liquid level and the ballast sleeve 64 will exert a smaller downward pressure against the buoyancy pressure of the float chamber 46. This relationship between the portion of the ballast sleeve 64 above the liquid level and the buoyancy pressure created by the float chamber 46 provides an overall operational pressure in the suction control chamber 16 which is within the typical operating ranges of a chest drainage device 10 while allowing the overall height of the suction control chamber 16 to be reduced.

By maintaining the preferred density of the ballast sleeve 64 at or near the density of water, the relationship between the portion of the ballast sleeve 64 above the liquid level and the buoyancy pressure of the float chamber 46 also creates a suction control chamber 16 wherein a visually readable linear scale may be used on the side of the suction control chamber 16 so that the user may easily modify the desired patient vacuum pressure by adding or removing incremental amounts of liquid from the suction control chamber 16. If the density of the ballast sleeve 64 is decreased, the float chamber 46 would operate within a limited range of dynamic water heights and the operational range of the chest drainage device 10 would be reduced. A chest drainage device 10 of this type would be able to produce the desired vacuum pressures within a limited operational range such as between 15 and 20 cm. $H_2O$. If the density of the ballast sleeve 64 is increased, the float chamber 46 would operate over a larger range of dynamic water heights and therefore, the operational range of the chest drainage device 10 would be increased; however, the scale along the side of the suction control chamber 16 would be compressed such that it would be very difficult to accurately adjust the suction control chamber to provide the desired vacuum pressure to the patient's pleural cavity. Any small change in the amount of liquid in the suction control chamber 16 would dramatically alter the vacuum pressure applied to the patient.

The chest drainage device 10 of the present invention functions similar to other chest drainage devices and is described briefly herein to assist in understanding the overall operation of the present chest drainage device 10. Operation of the chest drainage device 10 of the present invention includes the preliminary steps of adding a predetermined amount of liquid to the water seal chamber 14 to create the water seal 38 and adding a predetermined amount of liquid to the suction control chamber 16 to a level sufficient to provide the desired patient vacuum pressure. Once the vacuum hose 70 is attached to the vacuum source 56 and the drainage tube 24 is attached to the patient's pleural cavity, the process of suctioning fluid from the patient's pleural cavity is begun. If the vacuum pressure from the vacuum source 56 exceeds the patient's prescribed vacuum level, atmospheric air is pushed into the suction control chamber 16 through the fill opening 44; into the first column 40 and past the float chamber 46 into the second column 42 to decrease the vacuum pressure actually applied to the pleural cavity of the patient.

During normal operation of the chest drainage device 10, the water seal 38 in the water seal chamber 14 may be drawn upwardly in the water seal column 30 whenever the patient inspires (negative pressure). The liquid will flow downwardly in the water seal column 30 and into the reservoir area 33 of the water seal chamber 14 whenever the patient breathes out (positive pressure). As the fluid is drawn from the patient's pleural cavity, the liquid is collected in the collection chamber 12 and any air or gasses drawn from the pleural cavity of the patient will flow through the water seal chamber 14 and into the vacuum source 56.

While the preferred form of the invention has been described with reference to one specific type of drainage device, it will be apparent that various changes and modifications thereto may be made without departing from the true scope of the invention as defined by the following claims. For example, the general shape or design of the float chamber 46 or ballast sleeve 64 may be readily modified to be adaptable for use with nearly any suction control chamber design as long as the float chamber is able to apply a buoyancy pressure against the equivalent of a first column and is moveable to allow air or liquid to flow between the respective columns. Additionally, it is readily anticipated that the suction control chamber of the present invention may be an integral part of a chest drainage device or a separate suction control chamber which may be attached to nearly any chest drainage device without substantial modification or alteration of the present invention.

What is claimed is:

1. A chest drainage device for removing liquids and gases from the body of a patient comprising,
   a collection chamber in flow communication with the body of patient wherein liquid from the body of a patient will be collected therein,
   a source of vacuum pressure in flow communication with the collection chamber to apply vacuum pressure to the body of a patient to draw fluids into said collection chamber,
   a liquid containing suction control chamber in flow communication with the atmosphere and the source of vacuum pressure, said suction control chamber having first and second columns therein and said first and second columns having top ends and bottom ends and wherein said bottom ends are in flow communication with each other and the top end of said first column is in flow communication with the atmosphere and the top end of said second column is in flow communication with the source of vacuum pressure, a float means in flow communication with the first column wherein the float means restricts the flow of liquid in the suction control chamber between the first and second columns, and a ballast means extending upwardly from said float means within said second column, whereby said float means and said ballast means selectively restrict flow communication between the source of vacuum pressure and the atmosphere.

2. The device of claim 1, wherein the float means comprises a float chamber in flow communication with the bottom end of said first column.

3. The device of claim 2, wherein the ballast means comprises a ballast sleeve substantially surrounding said first column.

4. The device of claim 1, wherein the ballast means has a density approximately equal to the density of the liquid in said suction control chamber.

5. The device of claim 4, wherein the float means comprises a float chamber which selectively blocks the bottom end of said first column in response to the difference between the vacuum pressure applied by the source of vacuum pressure to the float means and atmospheric pressure.

6. The device of claim 5, wherein the float means allows atmospheric air to be pushed into the suction control chamber through the first column when the vacuum pressure applied by the source of vacuum pressure is greater than the desired patient vacuum pressure.

7. The device of claim 1, wherein the float means comprises a float chamber movably positioned adjacent to the bottom end of the first column and the ballast means comprises a ballast sleeve in connecting relation with the float chamber and oriented in close association with said first column.

8. The device of claim 7, wherein the ballast sleeve consists of top and bottom sections and wherein the bottom section includes an opening therein to allow air from the atmosphere to flow from the first column into the second column.

9. The device of claim 1, wherein the liquid in the suction control chamber forms a dynamic water height between the first and second columns to resist the flow of air from the atmosphere into the suction control chamber and the float means provides an additive buoyancy pressure to resist the flow of air from the atmosphere into the suction control chamber.

10. The device of claim 9, wherein the float means restricts the flow of liquid from the second column into the first column.

11. An improved suction control chamber in flow communication with a collection chamber of a drainage device for removing fluids from the body of a patient, wherein the suction control chamber comprises a first column having top and bottom ends wherein said top end is in flow communication with the atmosphere, a second column having top and bottom ends wherein said bottom end is in flow communication with the bottom end of said first column and said top end is in flow communication with a source of vacuum pressure, and a float means and ballast means in flow communication with said first column to selectively restrict flow communication between the source of vacuum pressure and the atmosphere.

12. The suction control chamber of claim 11 wherein said suction control chamber has top and bottom ends and wherein a liquid is placed in said suction control chamber to at least partially submerge said float means and said ballast means in the liquid.

13. The suction control chamber of claim 12, wherein said float means selectively restricts flow communication between the bottom end of said first column and the second column when said float means is submerged in the liquid in said suction control chamber.

14. The suction control chamber of claim 13, wherein said float means comprises a float chamber and the ballast means comprises a ballast sleeve and wherein said float chamber is submerged in the liquid in said suction control chamber and said ballast sleeve is partially submerged in the liquid in said suction control chamber.

15. The suction control chamber of claim 11, wherein said first column is substantially enclosed in said second column and wherein said float means is enclosed in said second column adjacent to the bottom end of said first column.

16. The suction control chamber of claim 15, wherein said float means comprises a float chamber adjacent to the bottom end of the first column and the ballast means comprises a ballast sleeve extending upwardly from the float chamber adjacent to the first column.

17. The suction control chamber of claim 16, wherein said ballast sleeve includes top and bottom sections and said ballast sleeve substantially surrounds said first column.

18. The suction control chamber of claim 17, wherein said bottom section of said ballast sleeve includes an opening therein to allow flow communication between said first column and said second column.

19. The suction control chamber of claim 11, wherein said float means selectively restricts the flow communication between the source of vacuum pressure and the atmosphere by selectively obstructing an opening in the bottom end of said first column.

20. The suction control chamber of claim 11, wherein said suction control chamber is an integral part of a drainage device having a collection chamber and a water seal chamber therein.

21. The suction control chamber of claim 11, wherein said second column of said suction control chamber is in flow communication with a water seal chamber and a source of vacuum pressure and wherein said water seal chamber is in flow communication with a collection chamber to drain fluids from the body of a patient.

22. The suction control chamber of claim 11, wherein the bottom end of the second column includes a damper chamber adjacent to said float means.

23. An improved suction control chamber for use with a drainage device having a collection chamber and a water seal chamber, wherein the improvement comprises a liquid containing suction control chamber having a top and bottom section a first column having top and bottom ends wherein said top end is in flow communication with the atmosphere and said bottom end is partially submerged in the liquid in the bottom section of said suction control chamber a second column having top and bottom ends wherein said bottom end is in flow communication with the bottom end of said first column and said top end is in flow communication with a source of vacuum pressure and a collection chamber, a float means and ballast means in flow communication with the bottom end of said first column to selectively restrict flow communication between the source of vacuum pressure and the atmosphere, a damper chamber in the bottom of said second column and having an opening therein adjacent to the bottom end of said first column, and wherein said float means is movably positioned in at least a portion of the damper chamber and is normally submerged in the liquid in the bottom section of the suction control chamber.

24. The suction control chamber of claim 23, wherein the suction control chamber is comprised of a second column substantially enclosing the first column and a means for flow communication between the source of vacuum pressure and the collection chamber of the drainage device.

25. The suction control chamber of claim 23, wherein the float means includes a buoyant float chamber and the ballast means comprises a ballast sleeve and wherein the ballast sleeve extends upwardly from the float chamber to movably surround part of the first column.

26. The suction control chamber of claim 25 wherein the ballast sleeve includes an upper and a lower section wherein the lower section includes an opening therein to allow flow communication therethrough between the first and second columns.

27. The suction control chamber of claim 25 wherein the ballast sleeve has a density approximately equal to the density of the liquid in the suction control chamber.

* * * * *